(12) United States Patent
Kim et al.

(10) Patent No.: US 9,415,060 B2
(45) Date of Patent: Aug. 16, 2016

(54) GELATIN-BASED NANOPARTICLE COMPLEX FOR TUMOR-TARGETED DELIVERY OF SIRNA AND METHOD FOR PREPARING THE SAME

(71) Applicant: KOREA INSTITUTE OF SCIENCE AND TECHNOLOGY, Seoul (KR)

(72) Inventors: Kwang Meyung Kim, Seoul (KR); Sun Hwa Kim, Seoul (KR); Ick Chan Kwon, Seoul (KR); Ji Young Yhee, Gyeonggi-do (KR); Sojin Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/340,845

(22) Filed: Jul. 25, 2014

(65) Prior Publication Data
US 2015/0038690 A1    Feb. 5, 2015

(30) Foreign Application Priority Data
Aug. 5, 2013  (KR) .......................... 10-2013-0092712

(51) Int. Cl.
  *A61K 47/48*  (2006.01)
  *A61K 31/7088*  (2006.01)
  *A61K 31/713*  (2006.01)

(52) U.S. Cl.
  CPC ........... *A61K 31/7088* (2013.01); *A61K 31/713* (2013.01); *A61K 47/48292* (2013.01); *A61K 47/48784* (2013.01); *A61K 47/48884* (2013.01)

(58) Field of Classification Search
  CPC ............ A61K 31/7088; A61K 31/713; A61K 47/48292; A61K 47/48784; A61K 47/48884

USPC .......................................... 536/23.1; 514/774
See application file for complete search history.

(56) References Cited

U.S. PATENT DOCUMENTS

| 2007/0087059 A1 | 4/2007 | Everaerts et al. | |
| 2010/0144902 A1* | 6/2010 | Shu ........................ | C08G 75/04 514/774 |
| 2014/0315805 A1* | 10/2014 | Carmichael .......... | A61K 9/0085 514/8.3 |
| 2014/0341842 A1* | 11/2014 | Zarembinski .......... | A61K 47/36 424/85.1 |

FOREIGN PATENT DOCUMENTS

KR        1020120026897 A        3/2012

OTHER PUBLICATIONS

Jing Xu, et al; "Non-Condensing Polymeric Nanoparticles or Targeted Gene and siRNA Delivery", National Institutes of Health, May 2012, vol. 1 pp. 21-34.

* cited by examiner

*Primary Examiner* — Janet Epps-Smith
(74) *Attorney, Agent, or Firm* — Ladas & Parry LLP

(57) ABSTRACT

Disclosed is a gelatin-based nanoparticle complex for tumor-targeted delivery of siRNA for specific gene silencing in tumor cells. The gelatin-based nanoparticle complex includes: poly-siRNA chains whose ends are modified with thiol groups; and thiolated gelatin bound to the poly-siRNA chains through disulfide crosslinking and charge interactions. The gelatin-based nanoparticle complex is not degraded in the bloodstream and can be efficiently absorbed into tumor cells without cytotoxicity. The delivered siRNA can effectively silence target gene expression. Also disclosed is a method for preparing the gelatin-based nanoparticle complex.

8 Claims, 17 Drawing Sheets

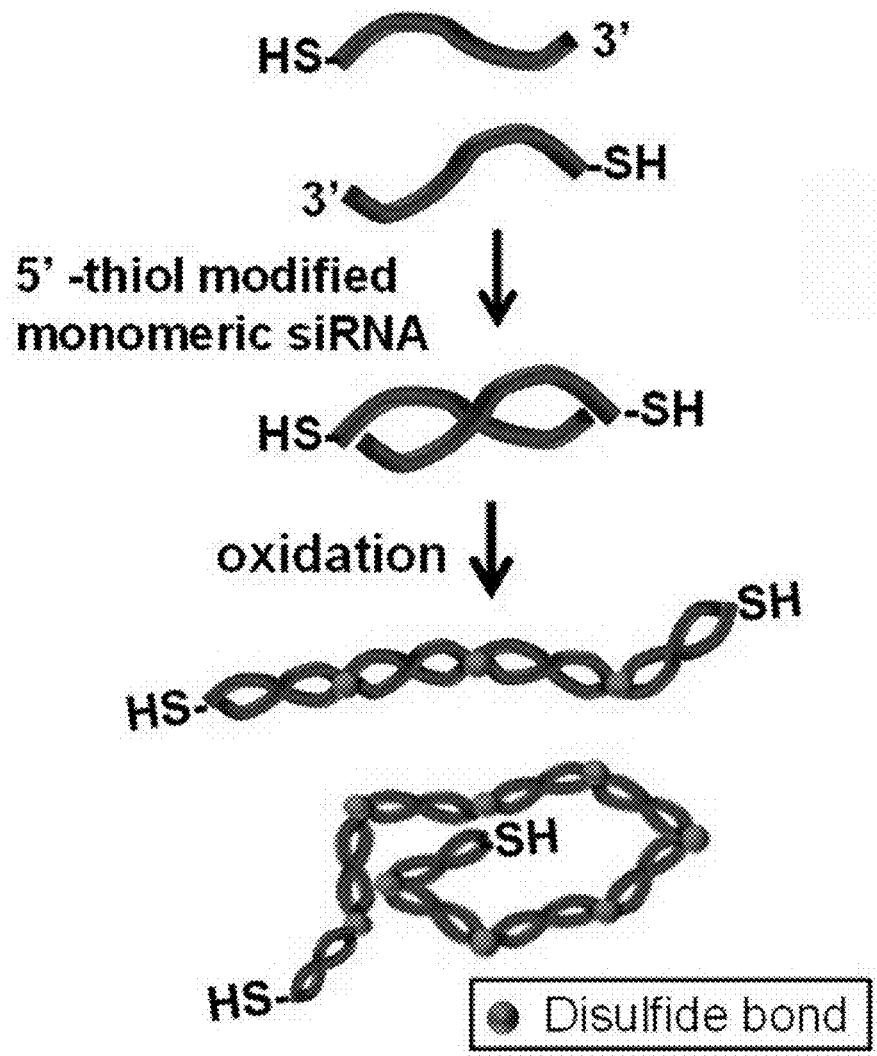

psi-tGel conjugates

↓ Self-cross-linking psi-tGel nanoparticles

SEQUENCE LISTING

```
<160> NUMBER OF SEQ ID NOS: 8

<210> SEQ ID NO 1
<211> LENGTH: 21
<212> TYPE: RNA
<213> ORGANISM: Artificial Sequence
<220> FEATURE:
<223> OTHER INFORMATION: sense sequence for red fluorescence
      protein-targeted siRNA
<220> FEATURE:
<221> NAME/KEY: misc_feature
<222> LOCATION: (20)..(21)
<223> OTHER INFORMATION: n is deoxythymidine

<400> SEQUENCE: 1
uguagaugga cuugaacucn n                                              21

<210> SEQ ID NO 2
<211> LENGTH: 21
<212> TYPE: RNA
<213> ORGANISM: Artificial Sequence
<220> FEATURE:
<223> OTHER INFORMATION: antisense sequence for red fluorescence
      protein-targeted siRNA
<220> FEATURE:
<221> NAME/KEY: misc_feature
<222> LOCATION: (20)..(21)
<223> OTHER INFORMATION: n is deoxythymidine

<400> SEQUENCE: 2
uguagaugga cuugaacucn n                                              21

<210> SEQ ID NO 3
<211> LENGTH: 21
<212> TYPE: RNA
<213> ORGANISM: Artificial Sequence
<220> FEATURE:
<223> OTHER INFORMATION: sense sequence for scrambled sequence of siRNA
<220> FEATURE:
<221> NAME/KEY: misc_feature
<222> LOCATION: (20)..(21)
<223> OTHER INFORMATION: n is deoxythymidine

<400> SEQUENCE: 3
```

```
ugaaguugca cuugaagucn n                                              21

<210> SEQ ID NO 4
<211> LENGTH: 21
<212> TYPE: RNA
<213> ORGANISM: Artificial Sequence
<220> FEATURE:
<223> OTHER INFORMATION: antisense sequence for scrambled sequence of
      siRNA
<220> FEATURE:
<221> NAME/KEY: misc_feature
<222> LOCATION: (20)..(21)
<223> OTHER INFORMATION: n is deoxythymidine

<400> SEQUENCE: 4
gacuucaagu gcaacuucan n                                              21

<210> SEQ ID NO 5
<211> LENGTH: 20
<212> TYPE: DNA
<213> ORGANISM: Artificial Sequence
<220> FEATURE:
<223> OTHER INFORMATION: forward primer

<400> SEQUENCE: 5
ggctgcttca tctacaaggt                                                20

<210> SEQ ID NO 6
<211> LENGTH: 20
<212> TYPE: DNA
<213> ORGANISM: Artificial Sequence
<220> FEATURE:
<223> OTHER INFORMATION: reverse primer

<400> SEQUENCE: 6
gcgtccacgt agtagtagcc                                                20

<210> SEQ ID NO 7
<211> LENGTH: 20
<212> TYPE: DNA
<213> ORGANISM: Artificial Sequence
<220> FEATURE:
<223> OTHER INFORMATION: forward primer

<400> SEQUENCE: 7
agagggaaat cgtgcgtgac                                                20

<210> SEQ ID NO 8
<211> LENGTH: 21
<212> TYPE: DNA
<213> ORGANISM: Artificial Sequence
<220> FEATURE:
<223> OTHER INFORMATION: reverse primer

<400> SEQUENCE: 8
caatagtgat gacctggccg t                                              21
```

GELATIN-BASED NANOPARTICLE COMPLEX FOR TUMOR-TARGETED DELIVERY OF SIRNA AND METHOD FOR PREPARING THE SAME

CROSS-REFERENCE TO RELATED APPLICATIONS

This application claims priority under 35 U.S.C. §119 to Korean Patent Application No. 10-2013-0092712 filed on Aug. 5, 2013 in the Korean Intellectual Property Office, the disclosure of which is incorporated herein by reference in its entirety.

BACKGROUND OF THE INVENTION

1. Field of the Invention

The present invention relates to a gelatin-based nanoparticle complex for tumor-targeted delivery of siRNA for specific gene silencing in tumor cells and a method for preparing the same.

2. Description of the Related Art

RNA interference (RNAi), a conserved mechanism for gene silencing, is a powerful therapeutic tool for treating various diseases including cancer. However, clinical application of small interfering RNA (siRNA) for RNAi is limited by the poor stability and inefficient cellular uptake of siRNA. The major challenge in siRNA therapy is to improve the efficiency of siRNA delivery.

Various carriers have been developed to effectively deliver siRNA. In general, strong cationic polymer-based nanoparticles have been widely considered as siRNA carriers. Although the cationic polymers showed high affinity for siRNA molecules to form nanoparticles through electrostatic interaction, the resulting nanoparticles usually have considerable toxicity and immunogenicity. Moreover, the cationic polymer-based vector systems commonly showed low target specificity in vivo that limited their clinical applications.

Recently, various structural modifications of siRNA molecules have attempted to overcome the inherent problems of siRNA delivery. Indeed, prudent modifications of the siRNA backbone improved its physicochemical properties for being incorporated in gene carriers without loss of gene-silencing efficacy. Modified siRNA, such as sticky siRNA and chemically modified polymerized siRNA (poly-siRNA), formed siRNA polymers through complementary $A_{5-8}/T_{5-8}$ 3' overhangs and chemical self-cross-linking. Compared to natural siRNA, the modified siRNA polymers showed enhanced delivery efficiency by forming condensed nanoparticles with various polymeric carriers, based on the higher molecular weight and increased charge density. Thus, the structurally modified siRNAs provide a wider variety of choice of vector systems for siRNA delivery, because these siRNAs show a higher binding affinity for carriers.

Proteins generally show low toxicity and high binding affinity for various drugs. The aqueous steric barrier of protein-based carriers allows low levels of reticuloendothelial system (RES) clearance, leading to improved pharmacokinetic properties. From this perspective, natural proteins are attractive materials as a potential gene carrier to achieve safe and efficient gene delivery. In particular, gelatin is a competitive candidate as a siRNA carrier. Gelatin can be simply modified with numerous functional groups, and it shows low cytotoxicity and antigenicity as a denatured form of collagen. Moreover, gelatin has great potential for in vivo application. The gelatin injection is commonly administered subcutaneously, but it can also be intravenously injected for a specific therapeutic purpose. In practice, Gelafundin and Gelafusal, which consist of gelatin derivates, are intravenously administered in the clinical setting. However, natural gelatin has not been used as a siRNA carrier because the loose complexes of gelatin and natural siRNA can be easily degraded in the bloodstream before RNAi performance.

SUMMARY OF THE INVENTION

The present invention has been made in an effort to solve the problems of the prior art and is intended to provide a gelatin-based nanoparticle complex that has high target specificity and resistance to degradation in the bloodstream without cytotoxicity and can deliver siRNA to target tumor cells, and a method for preparing the nanoparticle complex.

One aspect of the present invention provides a gelatin-based nanoparticle complex for tumor-targeted delivery of siRNA, including: poly-siRNA chains whose ends are modified with thiol groups; and thiolated gelatin bound to the poly-siRNA chains through disulfide crosslinking and charge interactions.

According to one embodiment of the present invention, the thiolated gelatin may be prepared by reacting gelatin with 10- to 50-fold molar excess of cystamine.

According to another embodiment of the present invention, the gelatin-based nanoparticle complex may include 1 part by weight of the poly-siRNA chains and 5 to 20 parts by weight of the thiolated gelatin.

According to another embodiment of the present invention, the poly-siRNA may have 21 to 1,000 base pairs (bp).

Another aspect of the present invention provides a method for preparing a gelatin-based nanoparticle complex for tumor-targeted delivery of siRNA, the method including: modifying a pair of complementary sequences of siRNA with thiol groups at the 5'-ends of the strands; mixing the pair of thiol-modified siRNA sequences with other pairs of thiol-modified siRNA sequences, followed by oxidation to form self-polymerized poly-siRNA chains; modifying gelatin with thiol groups to prepare thiolated gelatin; and reacting the poly-siRNA chains with the thiolated gelatin.

According to an embodiment of the present invention, the thiolated gelatin may be prepared by reacting gelatin with 10- to 50-fold molar excess of cystamine.

According to a further embodiment of the present invention, 1 part by weight of the poly-siRNA chains may react with 5 to 20 parts by weight of the thiolated gelatin to prepare the gelatin-based nanoparticle complex.

The gelatin-based nanoparticle complex for tumor-targeted delivery of siRNA according to the present invention is not degraded in the bloodstream and can be efficiently absorbed into tumor cells without cytotoxicity. The delivered siRNA can effectively silence target gene expression.

BRIEF DESCRIPTION OF THE DRAWINGS

These and/or other aspects and advantages of the invention will become apparent and more readily appreciated from the following description of the embodiments, taken in conjunction with the accompanying drawings of which:

FIGS. 1a to 1d are schematic diagrams showing a method for preparing a gelatin-based nanoparticle complex for tumor-targeted delivery of siRNA according to the present invention;

DETAILED DESCRIPTION OF THE INVENTION

Figure 1B:
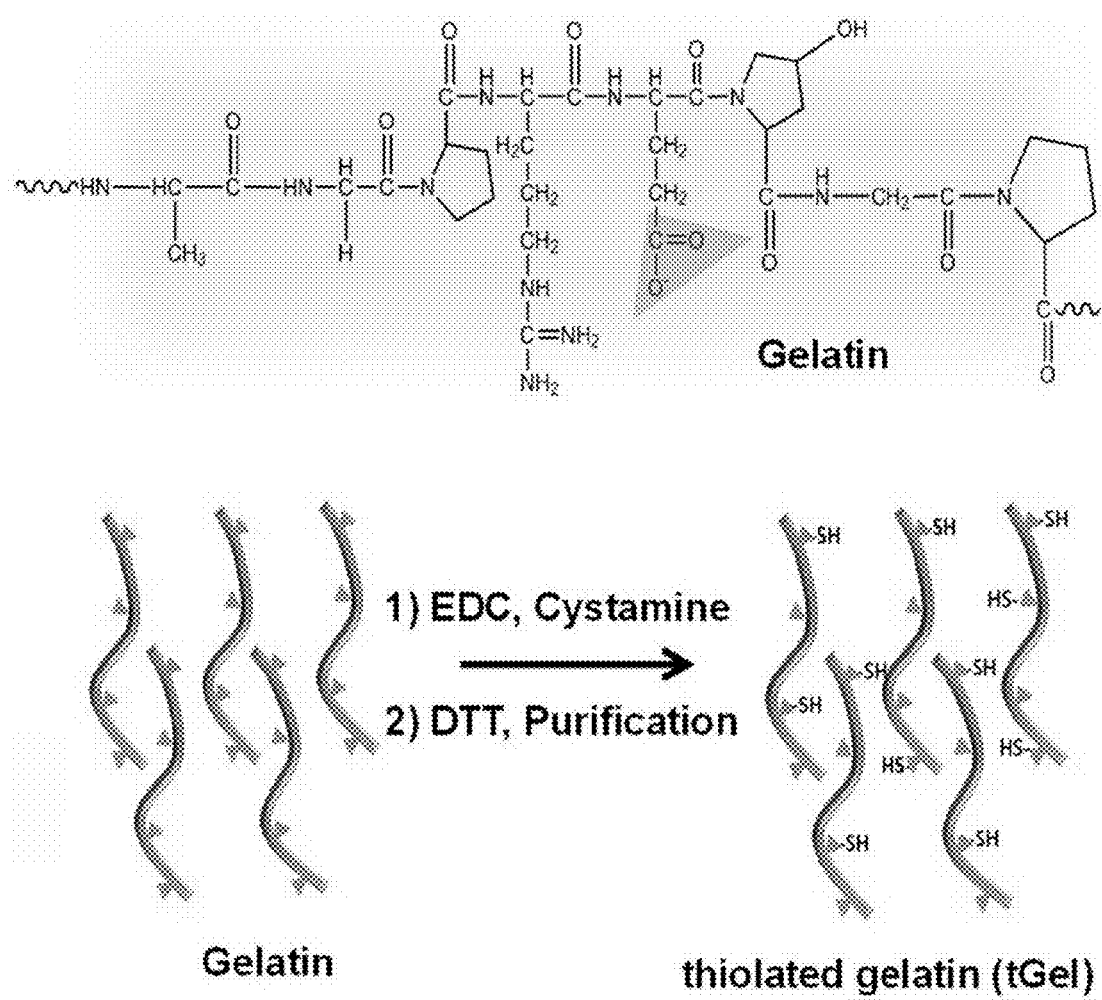

The present invention provides a new in vivo siRNA delivery system using biocompatible gelatin. Specifically, the siRNA delivery system of the present invention takes the form of a nanocomplex including gelatin and siRNA. To provide a sufficient binding affinity between gelatin and siRNA, both molecules are modified with thiol groups. The resulting thiolated gelatin (tGel) forms self-crosslinked gelatin nanoparticles, and the 5'-end thiol-modified siRNA is self-polymerized to form poly-siRNA. Subsequently, the thiolated gelatin is allowed to react with the poly-siRNA. As a result of this reaction, the poly-siRNA and the condensed thiolated gelatin nanoparticles form a complex.

Specifically, the gelatin-based nanoparticle complex of the present invention includes: poly-siRNA chains whose ends are modified with thiol groups; and thiolated gelatin bound to the poly-siRNA chains through disulfide crosslinking and charge interactions.

A suitable thiolating agent may be used for thiolation of the gelatin. The thiolating agent may be cystamine but is not limited thereto. The degree of thiolation of the gelatin can be controlled by varying the number of moles of cystamine reacting with the gelatin. Preferably, the gelatin reacts with 10- to 50-fold molar excess of cystamine. When the number of moles of cystamine is small, the degree of thiolation of the gelatin may be low. In this case, the poly-siRNA chains and the gelatin cannot completely form the desired complex. Meanwhile, if the degree of thiolation of the gelatin is excessively high, the thiolated gelatin may be spontaneously assembled into large micro-sized precipitates before reaction with the poly-siRNA.

As can also be seen from the Examples section that follows, the weight ratio of the thiolated gelatin to the poly-siRNA chains also affects the formation of the gelatin-based nanoparticle complex. Preferably, the gelatin-based nanoparticle complex includes 1 part by weight of the poly-siRNA chains and 5 to 20 parts by weight of the thiolated gelatin. If the relative weight of the thiolated gelatin is less than the lower limit defined above, the poly-siRNA chains and the gelatin cannot be used for complete complex formation, as described above. Meanwhile, if the relative weight of the thiolated gelatin is more than the upper limit defined above, the encapsulation efficiency of the poly-siRNA is undesirably lowered.

The poly-siRNA, which forms the complex with the thiolated gelatin, can be degraded to mono-siRNA in an intracellular reducing environment. Accordingly, the poly-siRNA chains of various lengths may be included in the gelatin-based nanoparticle complex. The poly-siRNA may be from about 21 bp to about 1,000 bp in length.

The present invention also provides a method for preparing a gelatin-based nanoparticle complex for tumor-targeted delivery of siRNA. The method of the present invention is schematically shown in FIGS. 1a to 1d. Referring to the figures, the method of the present invention includes modifying a pair of complementary sequences of siRNA with thiol groups at the 5'-ends of the strands, mixing the pair of thiol-modified siRNA sequences with other pairs of thiol-modified siRNA sequences, followed by oxidation to form self-polymerized poly-siRNA chains, modifying gelatin with thiol groups to prepare thiolated gelatin, and reacting the poly-siRNA chains with the thiolated gelatin. The final gelatin-based nanoparticle complex achieves specific gene silencing effects via an RNAi mechanism when administered to target tumor cells.

In the Examples section that follows, the poly-siRNA-thiolated gelatin nanoparticles (psi-tGel NPs) were characterized in terms of their physiochemical properties, resistance to enzymatic degradation, reducibility, gene delivery properties, in vivo biodistribution, and in vivo gene silencing effect. As a result, the psi-tGel NPs were verified to enable cancer-targeted delivery of siRNA to cells.

The present invention will be explained in more detail with reference to the following examples. However, these examples are provided to assist in understanding the invention and are not intended to limit the scope of the present invention.

EXAMPLES

Materials and Reagents

Type B gelatin (225 bloom, MW=40-50 KDa), cystaminedihydrochloride, 1,4-dithiothreitol (DTT), N-2-hydroxyethylpiperazine-N'-ethanesulfonic acid (HEPES), and ethylenediaminetetraacetic acid (EDTA) were purchased from Sigma (St. Louis, Mo.). Fluorescence dyes, Flamma Fluor-FPR675 (FPR675) and fluorescein isothiocyanate (FITC) isomer, were purchased from DKC (Seoul, Korea) and Sigma, respectively. RNase-free distilled water and Lipofectamine 2000 were purchased from Invitrogen (Carlsbad, Calif.). PCR reagents were obtained from Qiagen (Valencia, Calif.).

The 5'-ends of red fluorescence protein (RFP)-targeted siRNA for visualizing gene suppression were modified with thiol groups, followed by annealing to form a self-polymer: sense sequence, 5'-UGUAGAUGGACUUGAACUCdTdT-3' (SEQ ID. No. 1), and antisense sequence, 5'-GAGUUCAAG UCCAUCUACAdTdT-3' (SEQ ID. No. 2). For negative control, scrambled sequences of siRNA were prepared: sense sequence, 5'-UGAAGUUGCACUUGAAGUCdTdT-3' (SEQ ID. No. 3), and antisense sequence, 5'-GACU-UCAAGUGCAACUUCAdTdT-3' (SEQ ID. No. 4).

Synthesis of Polymerized siRNA (Poly-siRNA)

Two different sequences of siRNA (1 mg, 0.076 μmol) were modified with thiol groups at the 5'-ends of sense and anti-sense sequences to form self-polymerized siRNA polymers. Dithiol-modified siRNA molecules in ultrapure water were mixed with DTT to expose the free thiol groups. The solution was gently vortexed at room temperature for 1 h, and then was purified using a Nap-10 desalting column (GE Healthcare, Piscataway, N.J.) and lyophilized. The lyophilized sulfhydryl group exposed siRNA molecules were self-polymerized in HEPES buffer (10 mM, pH 8.0) under mild oxidative condition. The resulting poly-siRNA was electrophoresed on 8% polyacrylamide gel to confirm the molecular distribution of poly-siRNA. The gel was stained with ethidium bromide for 3 min and visualized using a Gel Imaging System (MiniBIS Pro, DNR Bio-Imaging Systems, Jerusalem, Israel). Each band fraction of poly-siRNA was semi-quantified using image analysis software to confirm the size distribution of poly-siRNA. The reducibility of the polysiRNA was investigated using the gel electrophoresis of 10 µg of poly-siRNA after DTT treatment (10 mM, 5 h).

Synthesis of Thiol-Modified Gelatin (tGel) as New siRNA Carrier

Gelatin was functionalized by introducing thiol groups to prepare self-crosslinked gelatin nanoparticles, which formed a complex with poly-siRNA. The tGel was synthesized with covalent modification of the carboxylic acid groups of gelatin. Briefly, 100 mg of gelatin was dissolved in 10 ml phosphate buffer and then incubated with varying amounts of 10-, 20-, and 50-fold molar excess of cystamine (ized $tGel_{10}$, $tGel_{20}$, and $tGel_{50}$, respectively). Cystamine (5 mg/ml phosphate buffer, varied amounts) was slowly added to gelatin (100 mg/10 ml), and 1.5 molar excess of EDC (5 mg/ml phosphate buffer) to cystamine was mixed in the solution. The mixture solution was gently stirred at room temperature for 2 h, and final elution was performed with DEPC using a desalting column (PD-10 desalting column; GE Healthcare). To reduce the disulfide bonds, each reaction mixture was incubated with 5 mg of DTT for 30 min and then purified again with gel filtration using the PD-10 column. The purified thiolated gelatin was lyophilized before use.

Preparation and Characterization of Poly-siRNA-Thiolated Gelatin Nanoparticles To form poly-siRNA-carrying tGelnanoparticles (psi-tGel NPs), poly-siRNA (1 µg/1 µl HEPES buffer) was mixed with each $tGel_{10}$, $tGel_{20}$, and $tGel_{50}$ at a weight ratio ranging from 5 to 20. The equivalent poly-siRNA was reacted with non-thiolated gelatin to determine the binding affinity of poly-siRNA and natural gelatin. All samples were incubated at 37° C. for 24 h with gentle vortexing. The complex formation was primarily confirmed in a gel retardation assay, and the size distribution of the various psi-tGel NPs was observed using dynamic light scattering (DLS, Spectra Physics Laser Model 127-35) at 633 nm and 25° C. The morphology of the nanoparticles was observed with TEM (CM 200 electron microscope, Philips), in which the nanoparticles were negatively stained with 2 weight % aqueous uranyl acetate.

To determine whether psi-tGel NPs can release functional monomeric siRNA molecules, the resulting psi-tGel complexes were treated with reducing reagent. Each psi-$tGel_{10}$, psi-$tGel_{20}$, and psi-$tGel_{50}$ was incubated in 10 mM of DTT at 37° C. for 5 h. The stability of the psi-tGel NPs was investigated in serum condition using optimized psi-tGel NPs. Equivalent amounts of naked poly-siRNA, poly-siRNA-gelatin mixture, and psi-tGel NPs were incubated in 50% rat serum containing PBS at 37° C. for 0 h to 48 h. After the incubation, disulfide linkages were cleaved with DTT treatment (10 mM) to compare the remaining RNA molecules of 21 bps.

Cellular Uptake of Psi-tGel NPs

Murine melanoma cells (B16F10) and RFP-expressing B16/F10 cells (RFP/B16F10) obtained from Kyungpook National University (Daegu, South Korea) were used in this example. The cytotoxicity of the psi-tTF NPs was evaluated using a 3-(4,5-dimethylthiazol-2-yl)-2,5-diphenyltetrazolium bromide (MTT) assay. The B16F10 cells ($5.0 \times 10^3$ cells in 96-well plates) were exposed to varying concentrations of psi-tGelNPs ranging from 7.3125 to 250.0 µg/mL for 48 h. The psi-tGel formulation included 31.25 nM to 1 µM of poly-siRNA, and the poly-siRNA-lipofectamine formulation (psi-LF) including equivalent poly-siRNA was also treated to compare the cytotoxicity of the tGel carrier with that of commercial agents for transfection. After the treatment of 20 µL of MTT solution, the cell viability was determined by measuring the optical absorbance differences at 570 nm.

Cellular uptake of psi-tGel NPs was visualized in murine melanoma cells (B16F10) after treatment with fluorescence dye-labeled nanoparticles. The fluorescence dye-labeled nanoparticles were prepared using FITC-labeled tGel and FPR675-labeled poly-siRNA. The FITC (0.2 mg, 0.6 µl) was chemically coupled to gelatin (20 mg, 0.08 µl) in the water/DMSO (1:1 v/v, 5 ml) condition for 3 h. Unreacted molecules were removed with the PD-10 desalting column and then thiol-modified. In addition, 1 mg of poly-siRNA was labeled with a near infrared fluorescence (NIRF) dye, FPR675 (0.2 mg, 0.6 µmole), according to the manufacturer's instructions. The B16F10 cells ($1.0 \times 10^5$ cells/35 mm cover glass bottomed culture plate) were exposed to the dual-fluorescence labeled psi-tGel NPs (5 µg/ml) for 2 h. The cells were washed twice with phosphate buffered saline (PBS) and fixed with formaldehyde-glutaraldehyde combined fixative for 10 min. The fixed cells were stained with 4',6-diamidino-2-phenylindole (DAPI) for the nuclei and observed using a confocal laser scanning microscopy (LSM 510 META NLO, Carl Zeiss, Germany).

In Vitro Gene Silencing of Psi-tGel NPs

The gene silencing effect was visualized in RFP/B16F10 cells. The RFP/B16F10 cells were cultured in 6-well plates at a density of $2.0 \times 10^5$/well and stabilized in serum-free transfection media for 1 h before transfection. The cells were treated with naked RFP poly-siRNA, scrambled poly-siRNA-$tGel_{50}$ (psi(sc)-tGel), psi(RFP)-$tGel_{20}$, and psi(RFP)-$tGel_{50}$ for 4 h, respectively. The final concentration of poly-siRNA was adjusted to 100 nM. After 24 h of incubation, RFP expression in the cells was observed using fluorescence microscopy (IX81-ZDC, Olympus, Japan). In addition, reverse transcription-polymerase chain reaction (RT-PCR) was performed to quantitatively analyze gene expression. The total RNA was extracted from the cells using an RNeasy Mini kit (Qiagen) to reverse transcribe into cDNA using Multi-Scribe Reverse Transcriptase (Applied Biosystems, Foster City, Calif.). Using primers, the RFP sequences (forward: 5'-GGCTGCTTCATCTACAAGGT-3' (SEQ ID. No. 5) and reverse: 5'-GCGTCCACGTAGTAGTAGCC-3' (SEQ ID. No. 6)) in PCR produced a target amplicon of 245 bp. The relative expression level of RFP mRNA was normalized to β-actin mRNA, and the primer for β-actin was as follows: forward, 5'-AGAGGGAAATCGTGCGTGAC-3' (SEQ ID. No. 7), and reverse, 5'-CAATAGTGATGACCTGGCCGT-3' (SEQ ID. No. 8)). Amplification was performed for 25 cycles, and the PCR products were separated on 2% agarose gels.

In Vivo and Ex Vivo NIRF Imaging of Psi-tGel NP-Injected Tumor-Bearing Mice

All animal experiments were performed in compliance with the relevant laws and institutional guidelines of the Korea Institute of Science and Technology (KIST). To avoid fluorescence interference by the melanin pigment and RFP of the B16F10 cells, squamous cell carcinoma (SCC-7) tumor-bearing mice were prepared for monitoring in vivo biodistribution of optimized psi-tGel NPs. SCC-7 cells ($1.0 \times 10^6$ cells/head) were injected subcutaneously into male athymic nude mice (n=6, Oriental Bio Inc., Seoul, Korea). Fourteen days post-inoculation, FPR675-labeled poly-siRNA or FPR675- labeled psi-tGel$_{50}$ was intravenously injected into the mice at an equivalent dose of 50 μg of poly-siRNA/head. Real-time in vivo fluorescence of FPR675 was monitored using the eXploreOptix system (Advanced Research Technologies, Montreal, Canada) for 24 h. The fluorescence intensity at each tumor region was calculated using the region of interest (ROI) function of Analysis Workstation software (ART Advanced Research Technologies, Montreal, Canada). The mice were euthanized at 24 h post-injection, and the fluorescence of FPR675 of the excised tumors and internal organs was observed using a 12-bit CCD camera (Image Station 4000 MM; Kodak, New Haven, Conn.).

In Vivo Gene Silencing of Psi-tGel NPs in RFP/B16F10 Tumor-Bearing Mice

In vivo gene silencing of psi-tGel NPs was visualized in RFP/B16F10 tumor-bearing mice. The RFP/B16F10 tumor-bearing mice (n=9) were also prepared with subcutaneous inoculation of RFP/B16F10 cells ($1.0 \times 10^6$ cells/head) in athymic nude mice. The mice were divided into 3 tumor-RFP matched groups when the tumor volume reached 65 mm$^3$. The mice in each group received psi(sc)-tGel$_{50}$, psi(RFP)-tGel$_{50}$ (40 μg of poly-siRNA/head), and saline, respectively. The psi-tGel NPs and saline were all intravenously injected on day 0, day 2, and day 4. The changes in tumor fluorescence for RFP expression were monitored for 5 days, and all mice were euthanized to isolate the tumor tissues to compare the fluorescence intensity of the excised tumors. In addition, total RNA was extracted from the tumor tissues using the RNeasy-Plus Mini kit (Qiagen), and reverse transcriptase PCR (RT-PCR) was performed to semi-quantitatively analyze RFP gene expression. Changes in body weight and behavioral abnormalities were monitored to observe the signs and symptoms of systemic toxicity. Histologic examination of major visceral organs was also performed after the experiment.

Statistics

The differences in cell viability, fluorescence intensity at tumor, and relative tumor RFP expression were analyzed by using Student's t-test for pairs of control and psi-tGel NPs-treated groups. A p-value less than 0.05 were considered statistically significant. All statistical analyses were performed using the software SPSS (version 11.0, SPSS, Chicago, Ill.).

Results and Discussion

Synthesis and Characterization of Psi-tGel NPs

Figure 1C:
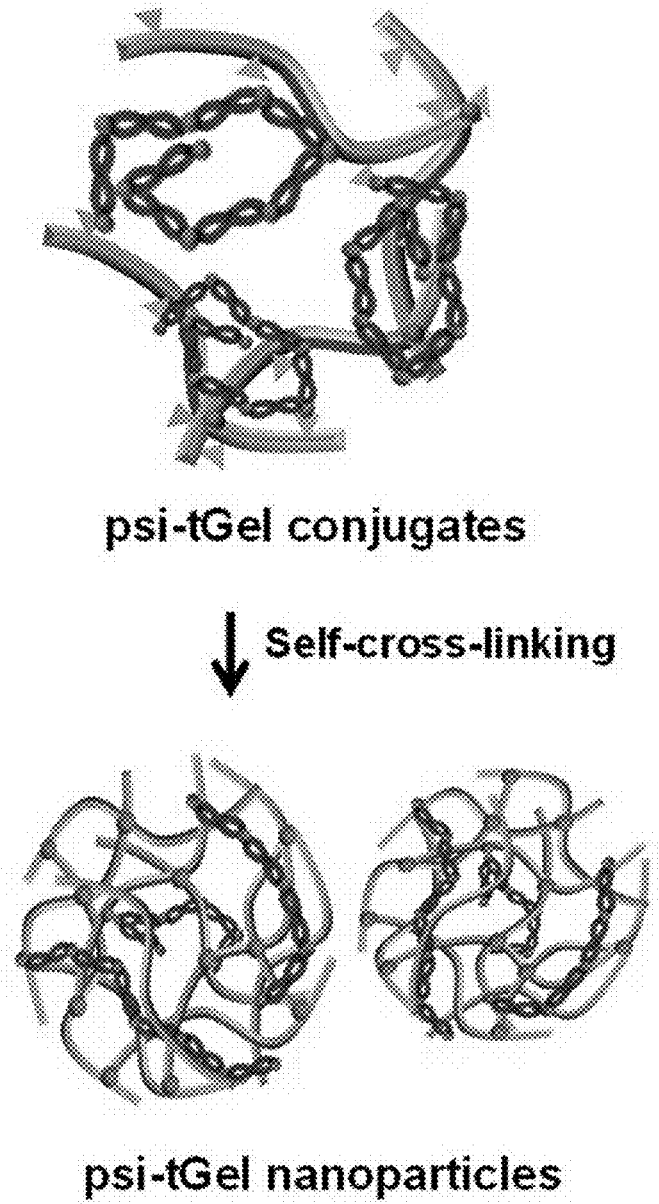
Figure 1D:
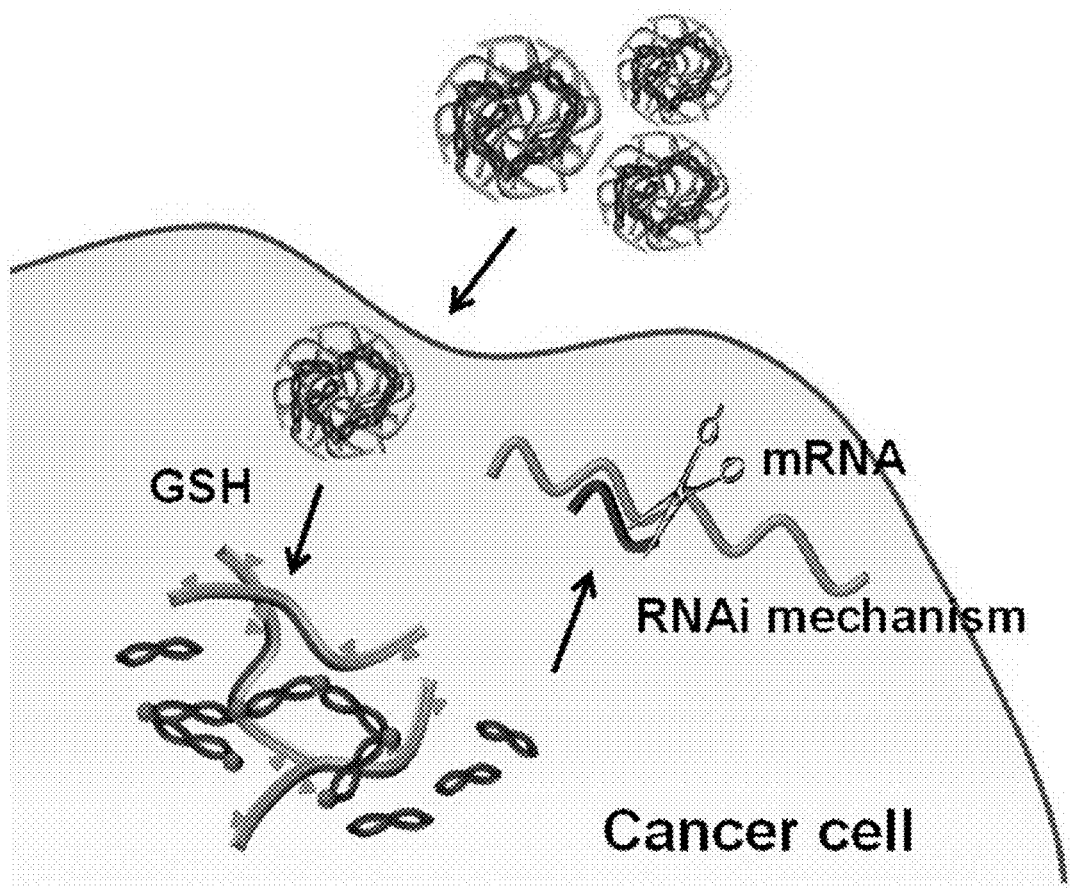

In the present invention, gelatin-based nanoparticles for siRNA delivery were synthesized as shown in FIGS. 1a to 1d. First, poly-siRNA was synthesized using 5'-end thiol-modified sense and anti-sense strands of siRNA (FIG. 1d). The thiol-modified siRNA molecules were self-polymerized through disulfide bonds. Second, natural gelatin was also modified using cystamine (FIG. 1b). The poly-siRNA and tGel were expected to form psi-tGel conjugates through the disulfide crosslinking reaction and partial charge interactions. On average, gelatin included 8% arginine, 4% lysine, and 1% histidine, which are positive charged amino acid residues, and poly-siRNA with increased anionic charge density interacts with these amino acid residues. The sulfhydryl groups on tGel and poly-siRNA contribute to further crosslinking to form psi-tGel NPs (FIG. 1C). These psi-tGel NPs are localized at tumor sites with an enhanced permeation and retention (EPR) effect and release functional monomeric siRNA molecules in the cancer cell cytoplasm (FIG. 1d).

Figure 2A:
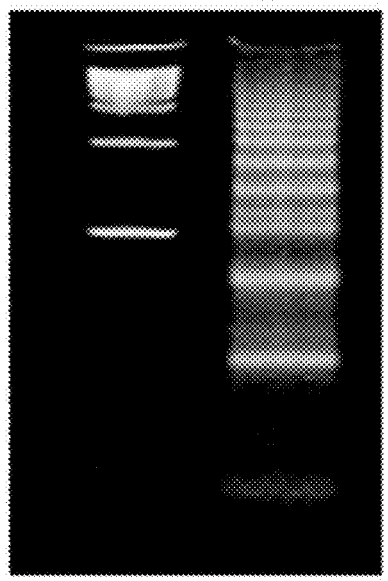
FIGS. 2a to 2g show data regarding the physicochemical properties of gelatin-based nanoparticle complexes (psi-tGel NPs) according to embodiments of the present invention.
Figure 2B:
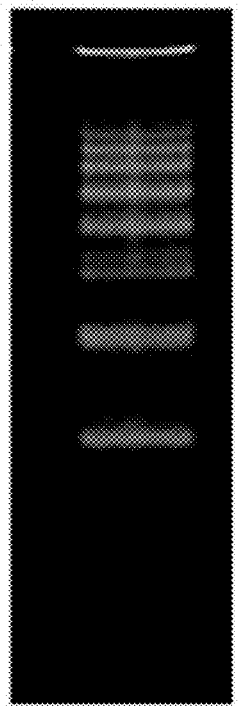
Figure 2C:
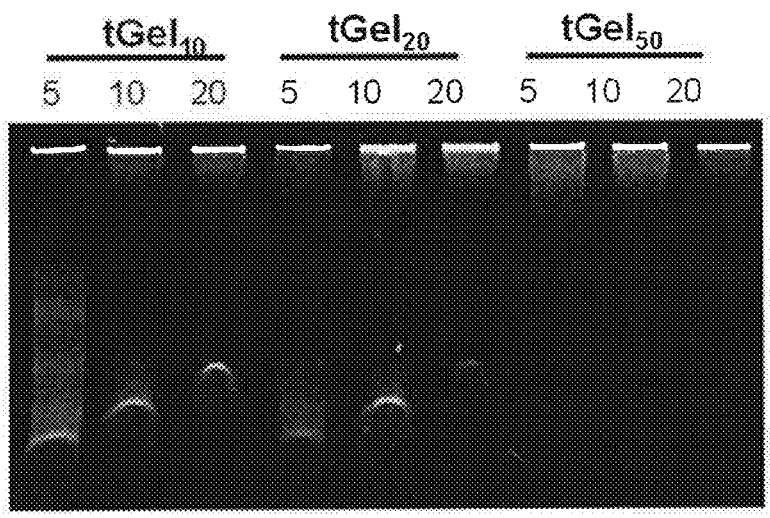

The synthesized poly-siRNA showed a ladder-like pattern in 8% polyacrylamide gel, indicating molecular weight distribution of siRNA polymers (FIG. 2a). The molecular weight distribution of the poly-siRNA was between 21 bp and 1,000 bp. Each band fraction of poly-siRNA was quantitatively analyzed, and 52.8% of poly-siRNA molecules were above 200 bp. On average, poly-siRNA showed 8 times more anionic charges per one molecule compared to typical monomeric siRNA. Although the siRNA molecules were successfully self-polymerized to give a higher molecular weight and charge density, the binding affinity of poly-siRNA and natural gelatin was not sufficient that unbound siRNA molecules were observed in the gel retardation assay (FIG. 2b). Therefore, in the present invention, gelatin was chemically modified with thiol groups to improve the binding affinity with poly-siRNA. The tGels were readily synthesized by conjugating 10-, 20-, and 50-fold molar excess of cystamine, resulting in tGel$_{10}$, tGel$_{20}$, and tGel$_{50}$, respectively. The resulting tGel polymers were incubated with poly-siRNA, and were spontaneously assembled. The poly-siRNA did not completely form complexes in tGel$_{10}$ NPs at a weight ratio of 1:5, 1:10, and 1:20 such that the tGel unbound siRNA molecules were observed in the gel retardation assay (FIG. 2c). The psi-tGel$_{20}$ also showed unbound siRNA at weight ratios 1:5 and 1:10, indicating incomplete formation of complexes. In contrast, all poly-siRNA was conjugated to tGel$_{20}$ at a 1:20 weight ratio. The psi-tGel$_{50}$ also formed complexes with whole siRNA molecules at a weight ratio ranging from 1:5 to 1:20.

Figure 2D:
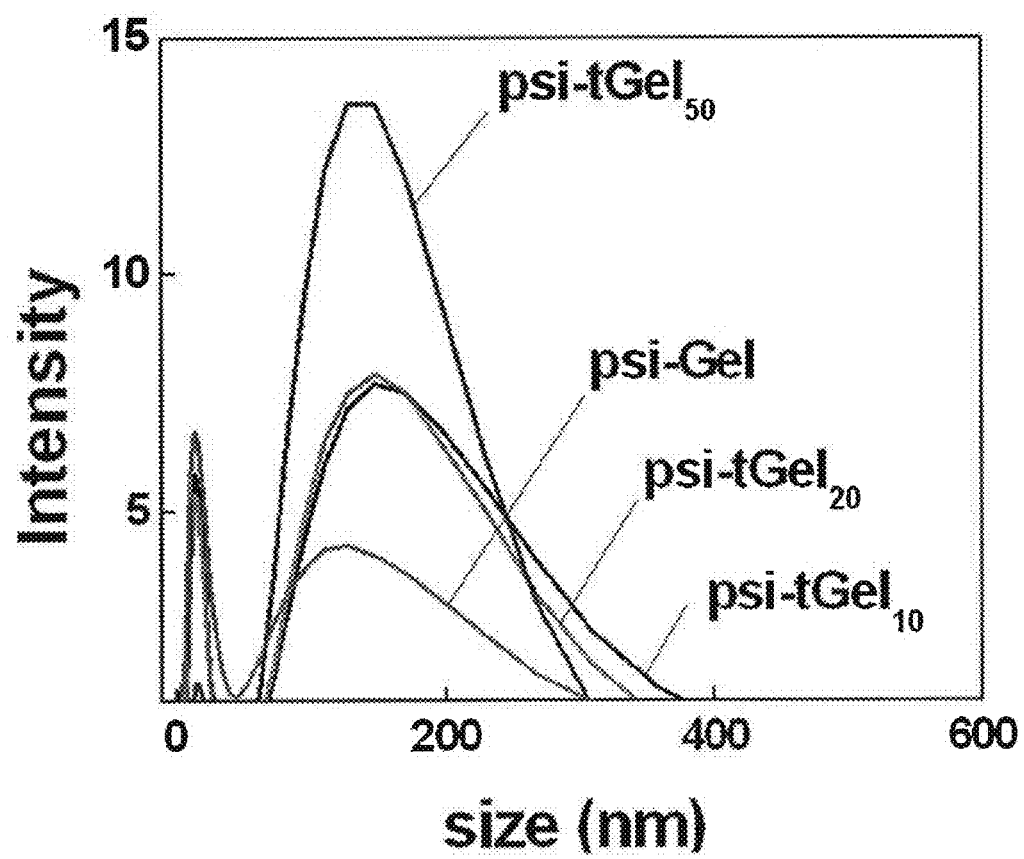
Figure 2E:
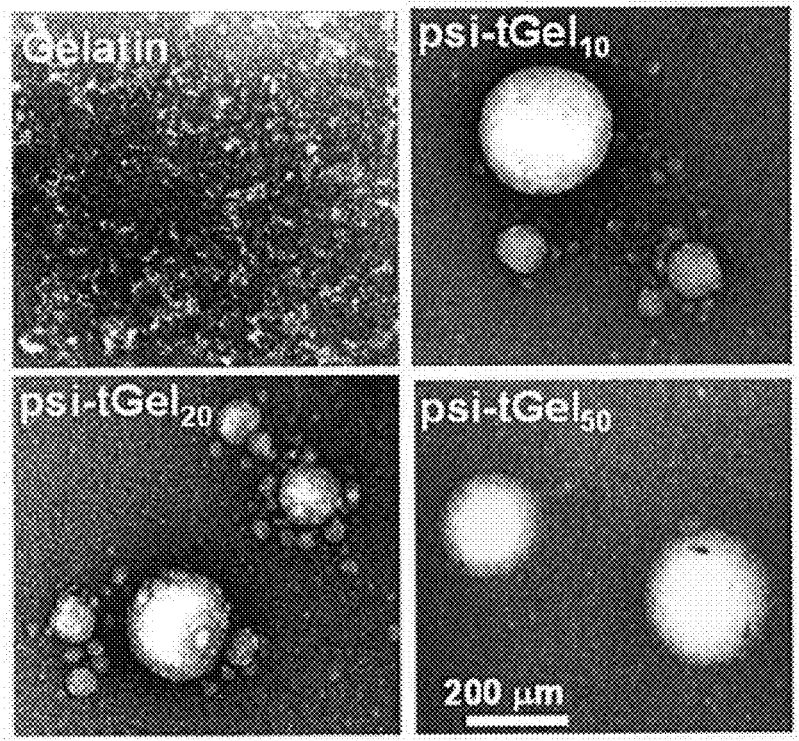

The particle size of the poly-siRNA/natural gelatin complexes (psi-Gel) and psi-tGels also supported that tGel$_{50}$ is the most appropriate for building up psi-tGel NPs. At the weight ratio 1:20, the psi-tGel$_{50}$ nanoparticles showed a sharp peak of 145 nm in the particle diameter. However, psi-Gel, psi-tGel$_{10}$, and psi-tGel$_{20}$ showed bimodal particle size distribution of 10 nm and 150 nm (FIG. 2d). In the TEM images, natural gelatin was observed as amorphous granules of 12.3 nm (FIG. 2e). In contrast, the psi-tGel nanoparticles showed a compact spherical structure with an average diameter of around 200 nm (FIG. 2d). In particular, the resulting psi-tGel$_{50}$ nanoparticles showed clear and uniform nanoparticle structures. From these examples, it is concluded that the poly-siRNA and tGel$_{50}$ conjugates spontaneously self-crosslinked to form condensed psi-tGel$_{50}$ nanoparticles, resulting in psi-tGel NPs. To investigate the characteristics, the weight ratio for the optimized psi-tGel$_{20}$ and psi-tGel$_{50}$ was fixed at 1:20 in the following examples.

Figure 2F:
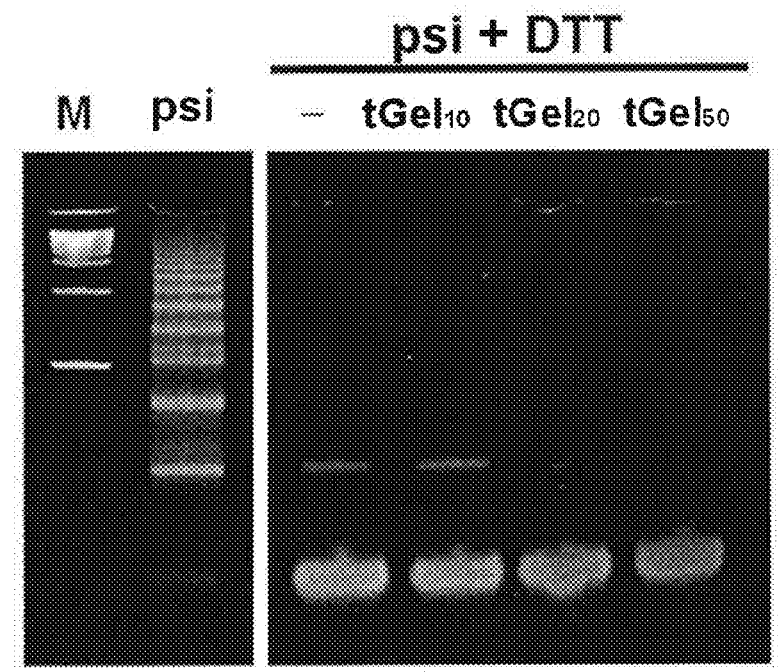
Figure 2G:
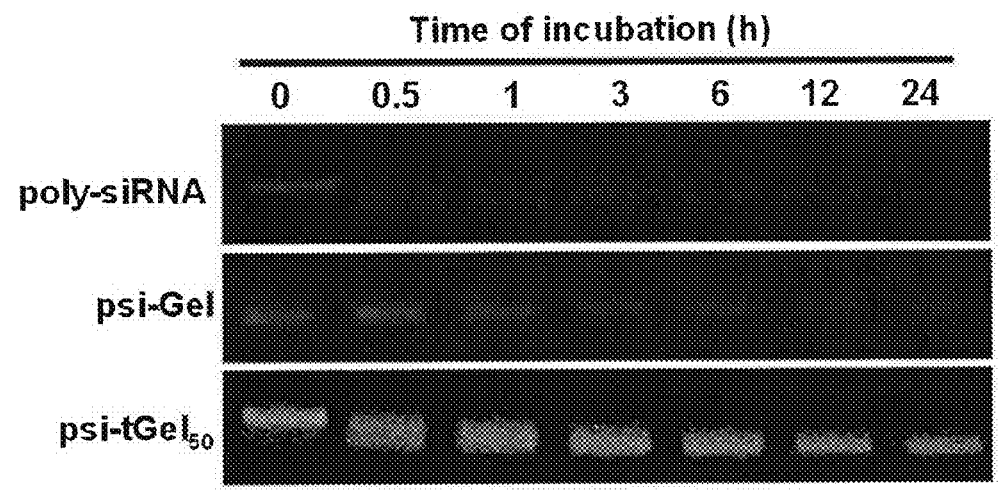

To successfully deliver functional siRNA, the psi-tGel NPs should be reversibly degraded under the reducing conditions. The inventors' previous study already demonstrated that the poly-siRNA synthesized by disulfide cross-linking could be degraded to mono-siRNA in the presence of a reducing reagent. Moreover, glutathione in the cytosol generally resulted in destabilization of disulfide bonds and dissociation of the thiol-conjugated nanoparticles. As animal cells include high levels of glutathione (5-10 mM) in cytosol, 10 mM of DTT was treated to reduce the psi-tGel NPs mimicking intracellular condition. After the treatment of 10 mM of DTT, a large amount of 21 bp siRNA molecules was observed in the polyacrylamide gel (FIG. 2f). This indicated that the disulfide bond in poly-siRNA and psi-tGel NPs could be reversibly reduced to release functional siRNA molecules in reductive conditions, such as in cytosols. In addition, the psi-tGel NPs protected the formulated siRNA molecules from degradation by nuclease. Most of the naked poly-siRNA was degraded within 30 min of incubation, whereas large amounts of siRNA molecules in 21 bp remained in the psi-tGel NPs for up to 24 h (FIG. 2g). These data show that the stability of siRNA molecules against the nuclease was enhanced by psi-tGel NP formulation, due to the successful complex formation of poly-siRNA with the nanoparticles. Therefore, the psi-tGel NPs would be stable in the blood circulation before cellular uptake in the target sites to deliver functional siRNA molecules for gene silencing.

Cytotoxicity and Cellular Uptake of the Psi-tGel NPs

Figure 3A:
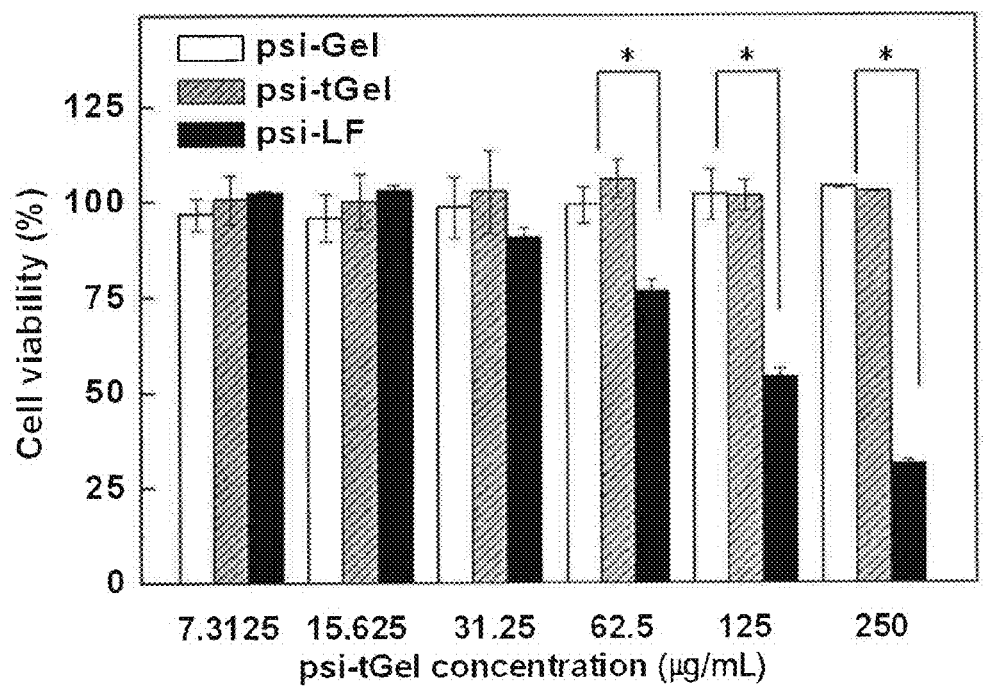
FIGS. 3a and 3b show data regarding in vitro cytotoxicity and cellular uptake of psi-tGel NPs.

The toxicity of siRNA carriers often limits the clinical application of siRNA. Lipofectamine, a commercial cationic liposome-based reagent, has been the most widely used for gene transfection. Although lipofectamine shows satisfactory transfection efficiency, liposome itself is toxic to certain cells, including primary cells. Gelatin is expected to be relatively non-toxic, and the cytotoxicity of tGel NPs was compared with poly-siRNA formulated in lipofectamine (psi-LF) at an equivalent dose of siRNA transfection. To determine the cytotoxicity of the psi-tGel NPs, an MTT assay in B16F10 was performed. The psi-LF showed considerable toxicity in the MTT assay at the concentration of >12.7 µg/mL psi-LF (>200 nM siRNA included formulation). At 200, 500, and 1,000 nM siRNA transfection doses for psi-LF formulation, the cell viability was 76.4%, 54.0%, and 24.2%. In contrast, the cell viability of the psi-tGel NPs at an equivalent dose for siRNA transfection was close to 100% (FIG. 3a). The psi-tGel did not show considerable toxicity at the 250 µg/mL concentration, which included 1 µM siRNA. This indicates that psi-tGel NPs have low toxicity at a high transfection dose, due to the neutral charge and natural polymer-based characteristics of psi-tGel NPs. These results are similar to the previously reported thiolated gelatin-based plasmid DNA delivery vector system for in vitro transfection. These results also implied that tGels have great potential as a carrier system for gene delivery with biocompatibility.

Figure 3B:
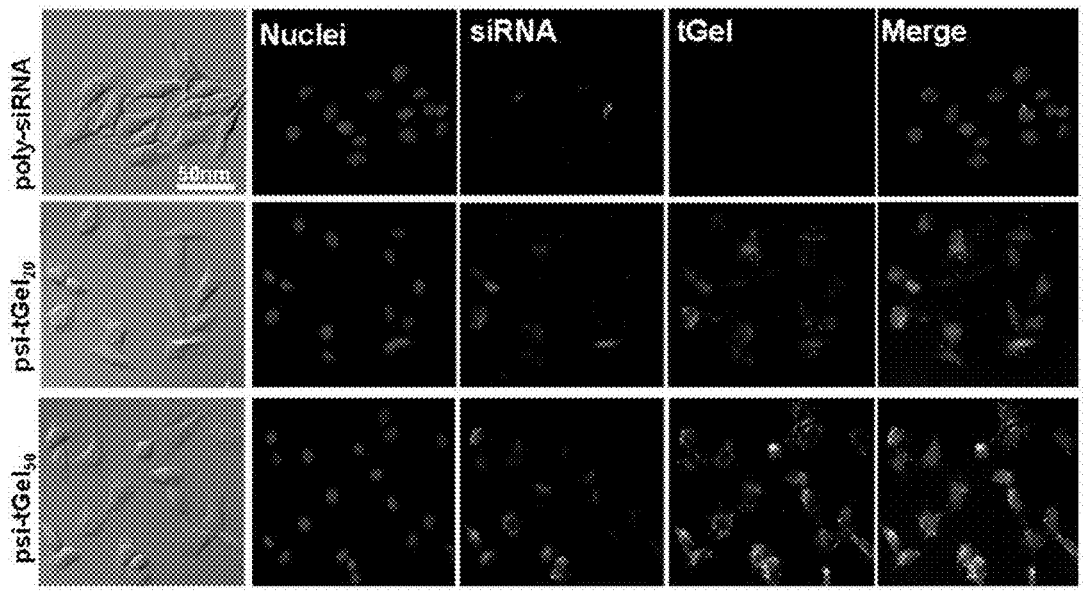

Based on the results of the cytotoxicity test, the poly-siRNA concentration in the psi-tGel NPs for the cellular uptake test was fixed at 62.5 nM siRNA (31.25 µg/mL of psi-tGel NPs). At this concentration, the naked FPR675-labeled poly-siRNA (red color) showed only marginal NIRF, indicating extremely low cellular uptake. However, the dual-labeled psi-tGel$_{20}$ and psi-tGel$_{50}$ NPs showed distinct fluorescence, resulting in intracellular delivery of psi-tGel NPs (FIG. 3b). Red and green spots of poly-siRNA and tGel were spread throughout the entire cytosol, and were mainly co-localized. The psi-tGel$_{50}$ NPs showed stronger fluorescence signals than the psi-tGel$_{20}$ NPs, suggesting efficient cellular uptake. The condensed NP structures play an important role in more favorable cellular uptake of psi-tGel$_{50}$ NPs.

In Vitro Gene Silencing of Psi-tGel NPs

Figure 4A:
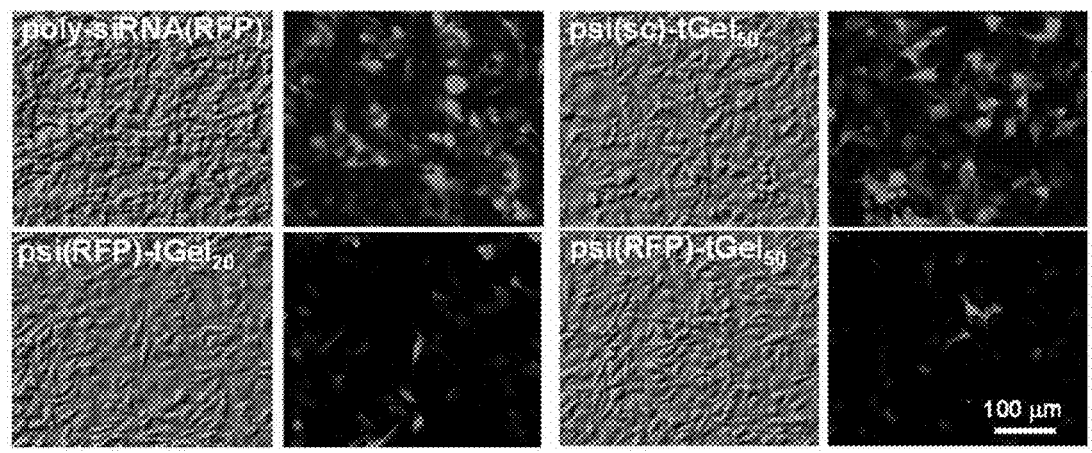
FIGS. 4a to 4c show data regarding in vitro gene silencing of psi-tGel NPs.
Figure 4B:
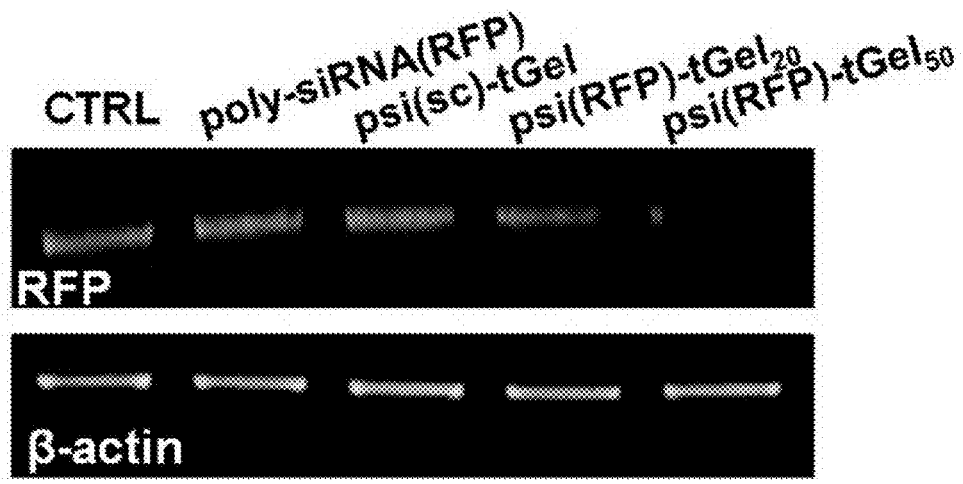
Figure 4C:
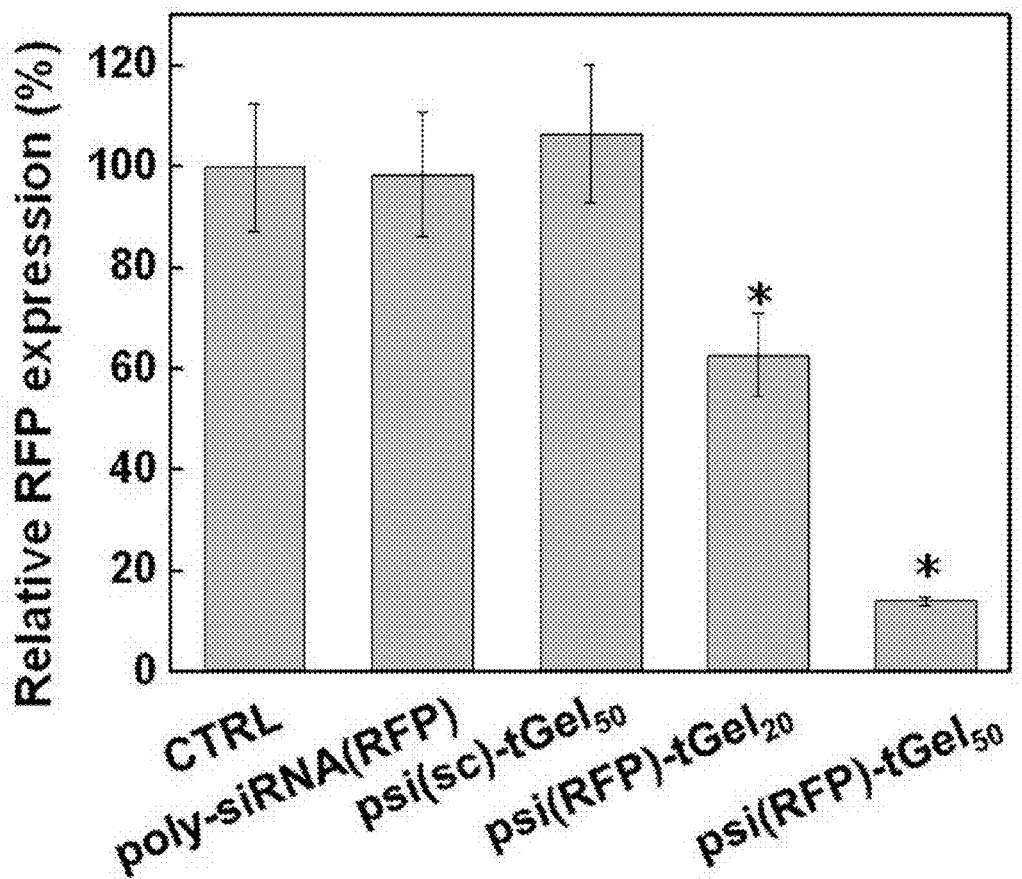

In vitro gene silencing was visualized in RFP/B16F10 cells. The naked poly-siRNA(RFP) and the psi(sc)-tGel$_{50}$-treated cells presented intense red fluorescence with RFP expression. In contrast, the psi(RFP)-tGel$_{20}$ and psi(RFP)-tGel$_{50}$-treated cells showed obviously reduced RFP expression (FIG. 4a). Particularly, the psi(RFP)-tGel$_{50}$ induced more effective RFP silencing than psi(RFP)-tGel$_{20}$. This is correlated with more efficient cellular uptake of psi(RFP)-tGel$_{50}$. For a quantitative analysis of RFP mRNA, RT-PCR was carried out with total RNA extracted from the cells. The RFP mRNA level in the cells was closely correlated with the observed RFP fluorescence (FIG. 4b). The naked poly-siRNA (RFP) and psi(sc)-tGel$_{50}$-treated cells showed no significant difference in RFP mRNA level with the control RFP/B16F10 cells. However, the RFP mRNA level was significantly reduced in the psi(RFP)-tGel-treated cells, and psi(RFP)-tGel$_{50}$ showed a better effect on target gene silencing than psi(RFP)-tGel$_{20}$ (FIG. 4c). These results verified the intracellular delivery of functional siRNA of the psi-tGel NPs. The delivered poly-siRNA molecules in the psi-tGel NPs were successfully reduced to mono-siRNA by cleaving the disulfide bonds in the cytosol, and the siRNA induced target gene suppression in the RFP/B16F10 cells. The psi-tGel NPs provided effective siRNA delivery in vitro, and the feasibility of using gelatin as a siRNA carrier was verified.

In Vivo Distribution of Psi-tGel NPs

Figure 5A:
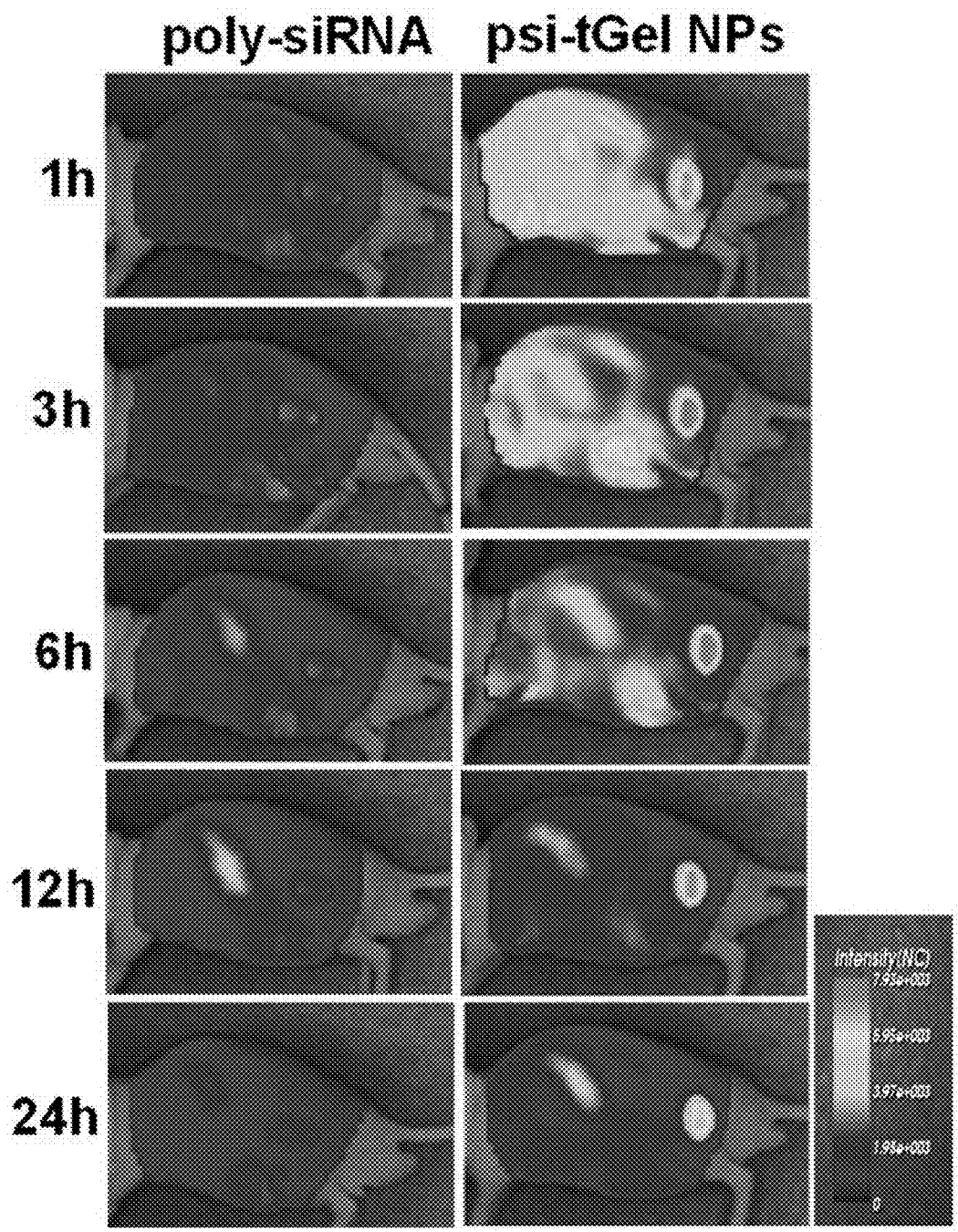
FIGS. 5a to 5d show the results of NIFR imaging to evaluate the biodistribution of psi-tGel NPs.
Figure 5B:
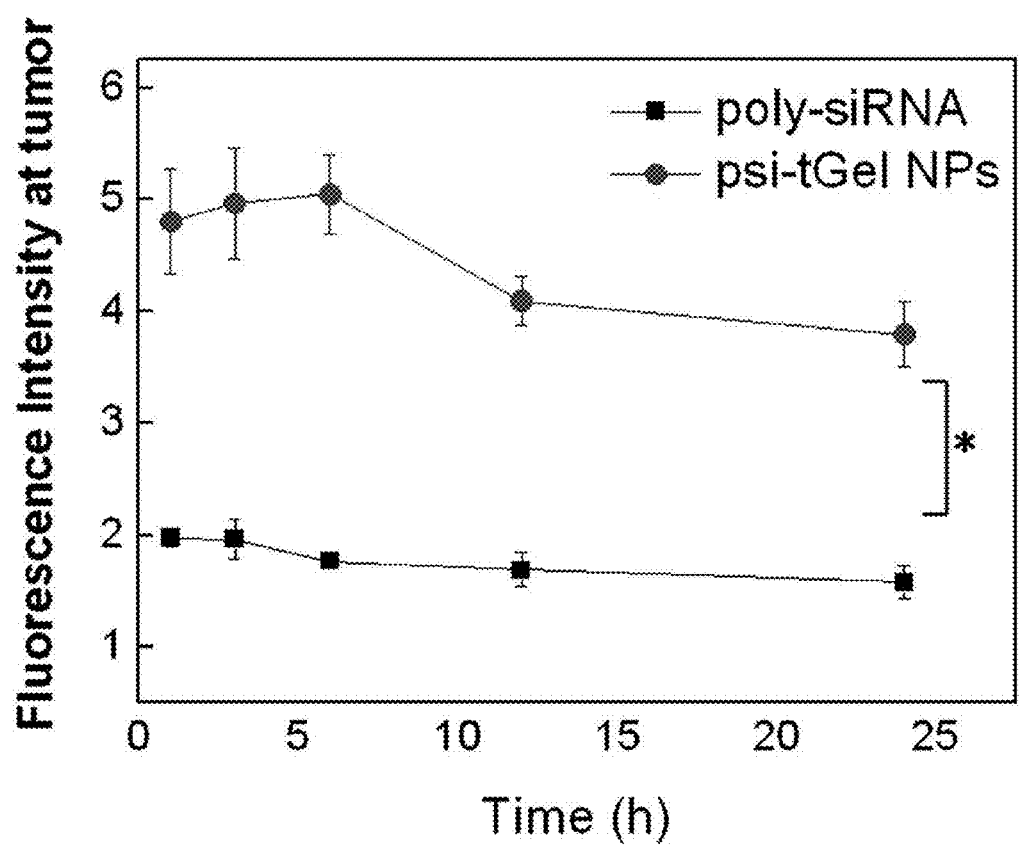

The psi-tGel NPs showed nano-sized structures, and it was expected that the psi-tGel could accumulate in tumors due to the EPR effect. Based on the results for in vitro cellular uptake and gene silencing, in vivo characteristics were investigated using psi-tGel$_{50}$ NPs. FPR675-labeled poly-siRNA was prepared for monitoring the in vivo pharmacokinetics of the naked poly-siRNA and the psi-tGel NPs, and non-invasive whole body NIRF imaging was performed after the injection. The tumor NIRF was not remarkably increased in the naked FPR675-labeled poly-siRNA-injected mice, but the psi-tGel NP-injected mice showed high tumor NIRF intensity, indicating tumor accumulation of psi-tGel NPs (FIG. 5a). The fluorescence at the tumor site gradually increased up to 6 h post-injection, and the tumor NIRF intensity was 2.8 times higher in psi-tGel NP-injected group than in the naked poly-siRNA-injected group (FIG. 5b).

Figure 5C:
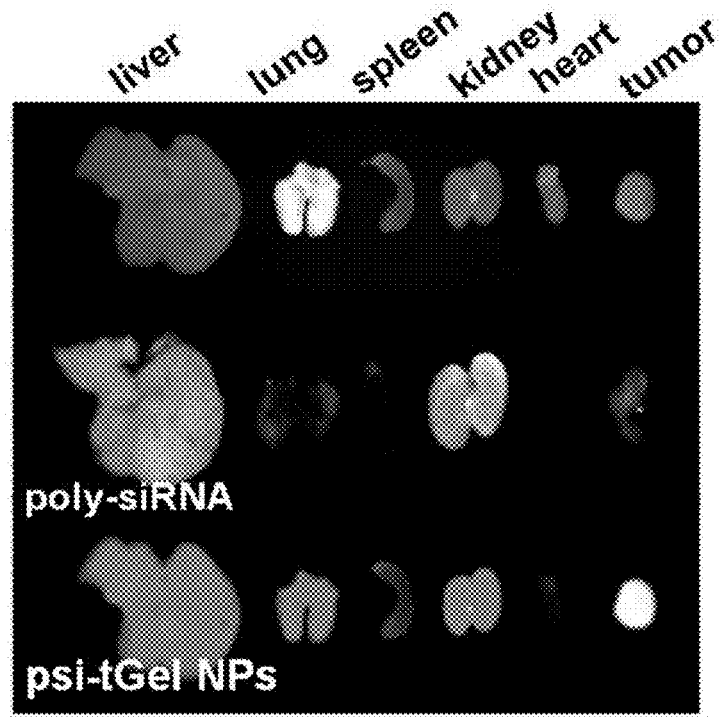
Figure 5D:
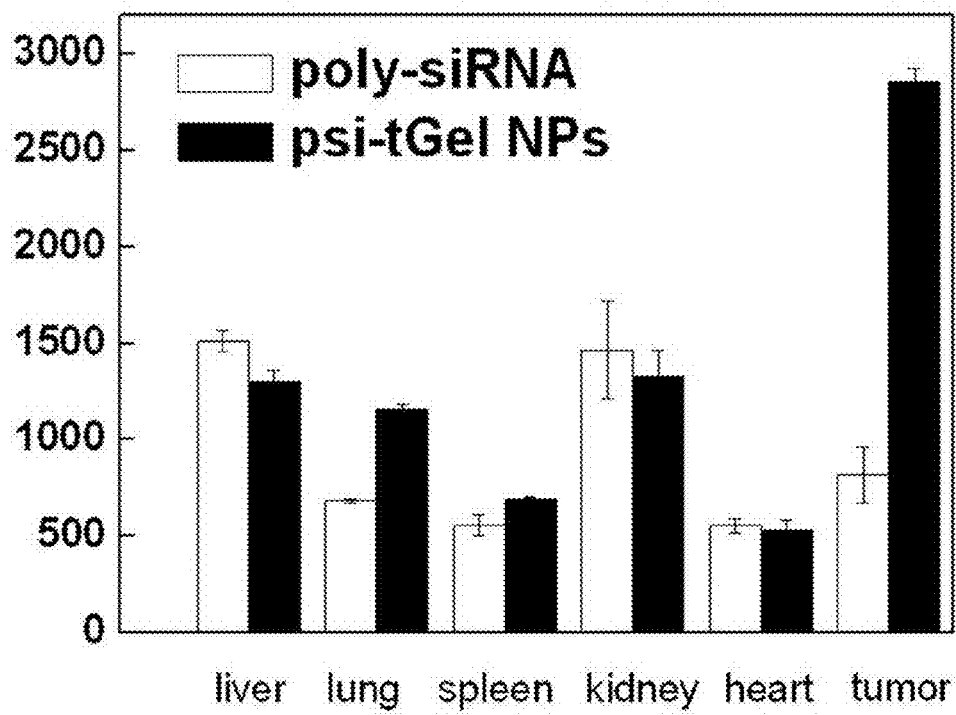

In the psi-tGel injected group, the excised tumors showed stronger fluorescence than the liver, lung, spleen, kidney, and heart (FIG. 5c). This was caused by tumor-targeted siRNA delivery of the psi-tGel NPs (FIG. 5d). This tumor accumulation property of psi-tGel NPs is due to the EPR effect, as other nanoparticles showed similar size distribution. Although defects in blood vessels are not consistent in various tumors, the increased capillary permeability of tumoral blood vessels generally allows the penetration of nanoparticles in the 50-200 nm size range. Thus, the tumor accumulation of psi-tGel NPs may be attributed to the particle size of 145 nm in diameter. Furthermore, relatively low NIRF intensity was recorded in the kidneys of the psi-tGel NP-injected mice. This implies that psi-tGel NPs circulate in the blood longer than naked poly-siRNA. Longer blood circulation also contributed to the accumulation of psi-tGel NPs in the target site.

In Vivo Gene Silencing of Psi-tGel NPs

Figure 6A:
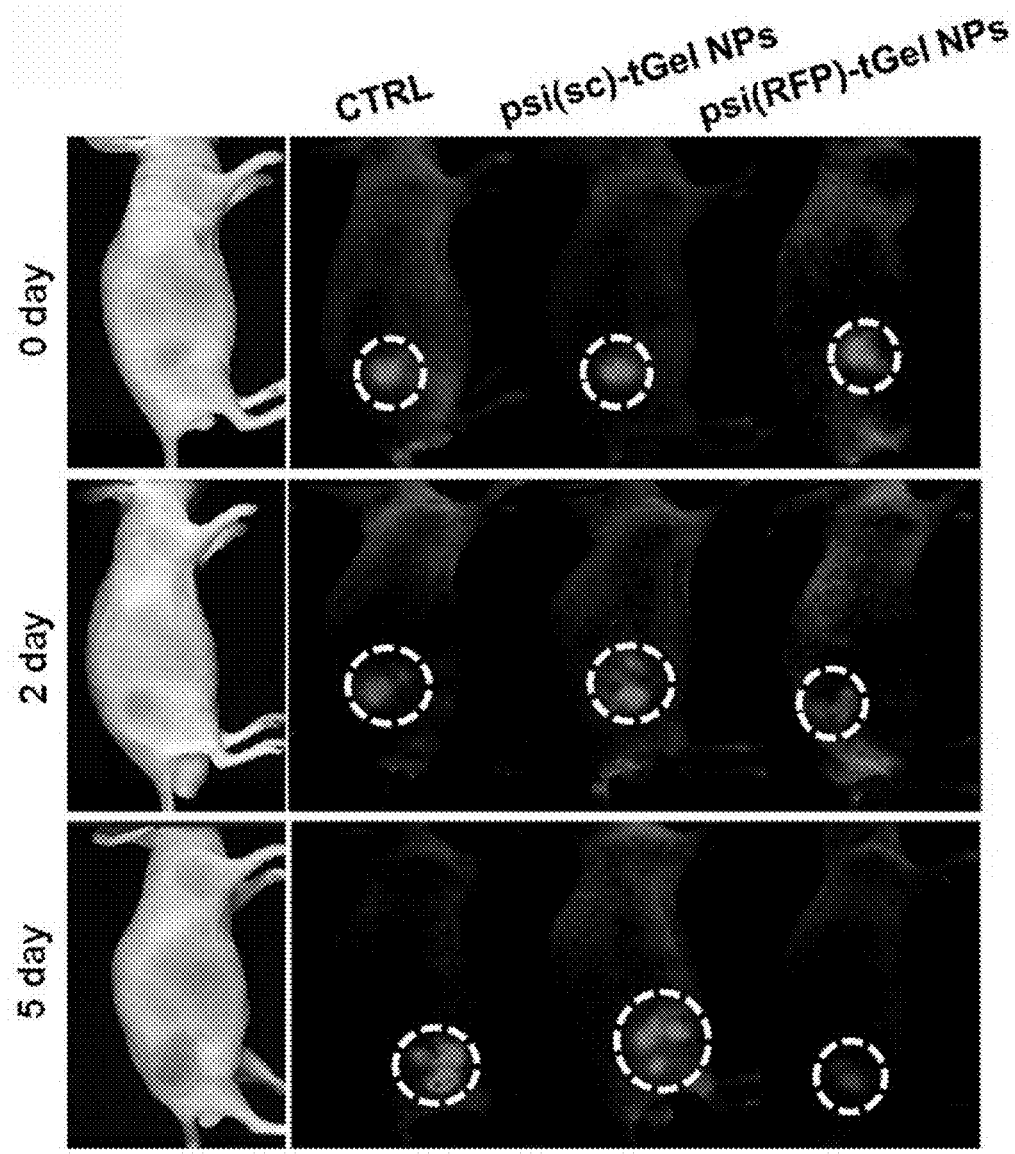
FIGS. 6a to 6d show data regarding in vivo gene silencing of administered psi(RFP)-tGel NPs in tumor-bearing mice.
Figure 6B:
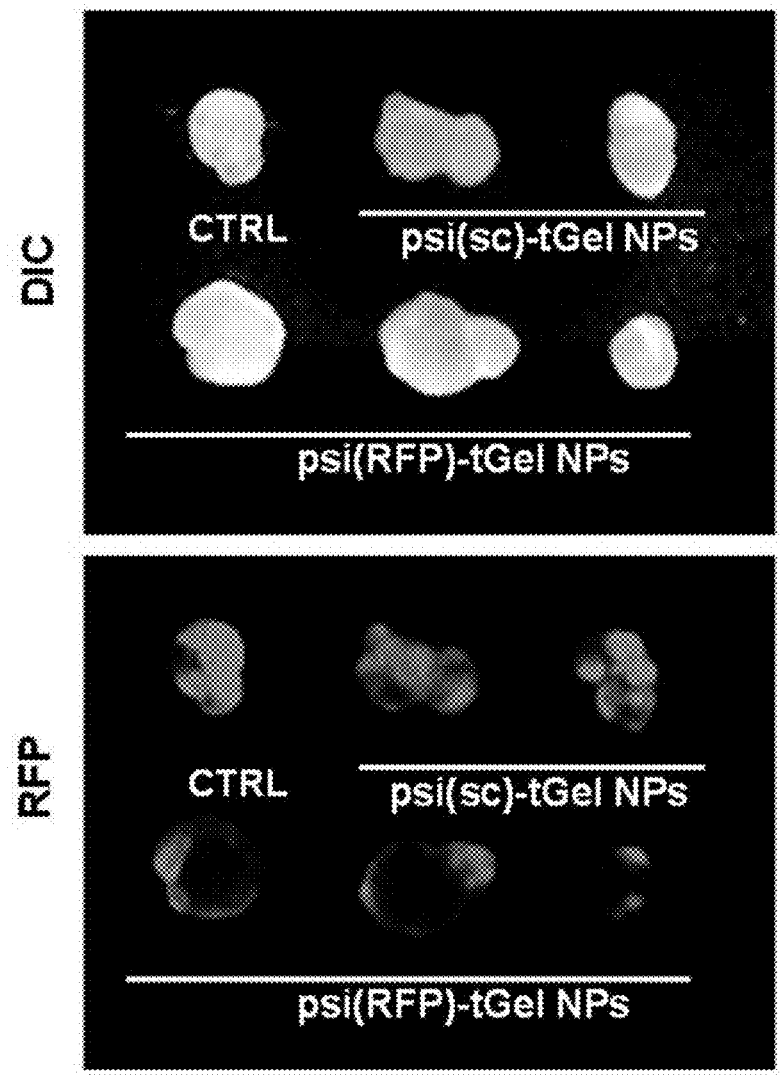

To provide substantive evidence of in vivo gene silencing of psi(RFP)-tGel NPs, tumor fluorescence images were non-invasively monitored in live RFP/B16F10 tumor-bearing mice for 5 days. The fluorescence intensity at the tumors was comparatively evaluated in groups of RFP-matched mice. The psi(sc)-tGel NP-injected mice retained intense RFP fluorescence at tumors compared to the control mice. In contrast, the psi(RFP)-tGel NP-injected group showed a remarkable reduction in RFP fluorescence at 2 days post-injection (FIG. 6a). In the excised tumors, RFP silencing of the psi(RFP)-tGel NPs was more clearly observed (FIG. 6b). These results revealed decisive evidence of tumor-targeted siRNA delivery of psi-tGel NPs, resulting in target gene silencing. RT-PCR confirmed that the tumor RFP of the psi(RFP)-tGel NP-injected group was significantly reduced at the mRNA level.

Figure 6C:
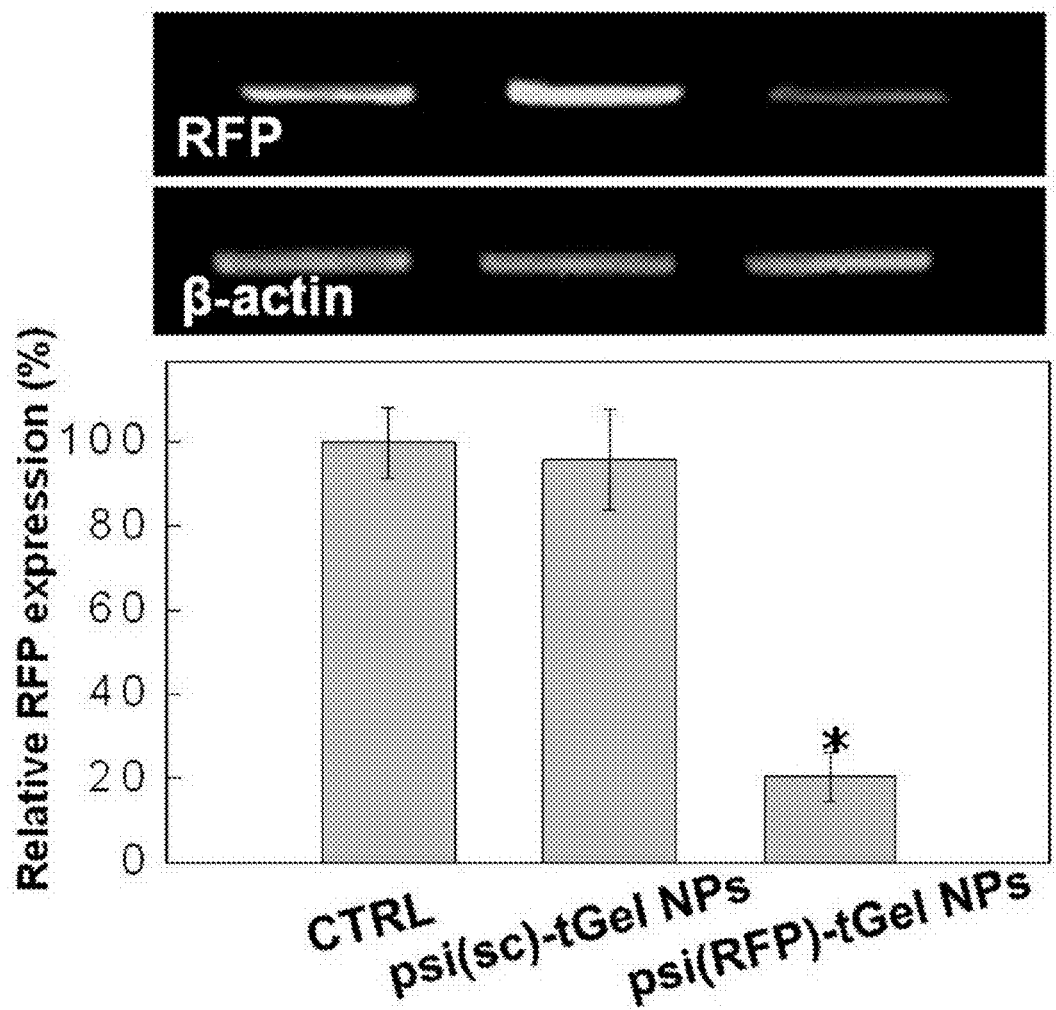

The tumors of the psi(sc)-tGel NP-treated group had a similar level of RFP mRNA in the PCR product, but the psi(RFP)-tGel NP-treated mice showed only 20.4% of RFP mRNA in tumors (FIG. 6c). The psi-tGel NPs can deliver functional siRNA molecules to tumors and can suppress the target gene via a sequence-specific RNA interference mechanism. Based on the tumor accumulation and efficient cellular uptake properties, the psi-tGel NPs achieved successful tumor-targeted siRNA delivery.

Figure 6D:
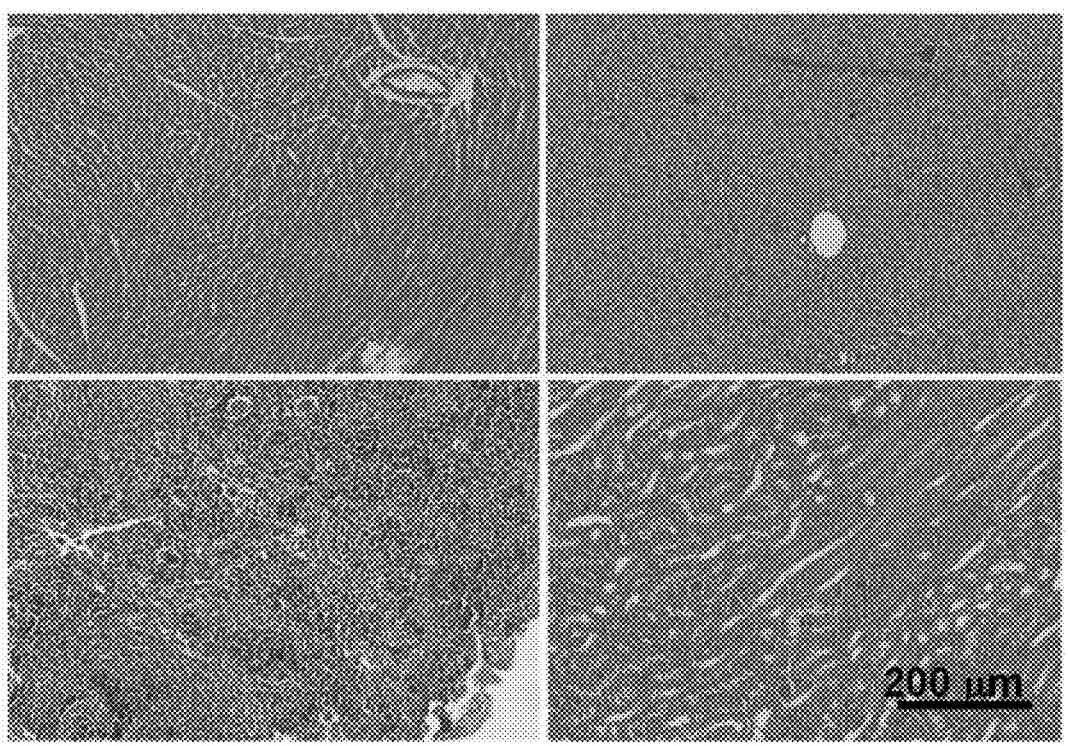

The psi-tGel NPs are also expected to be safe, because natural polymers usually offer excellent biocompatibility. In the present invention, the biocompatibility of psi-tGel NPs was finally verified. To evaluate the systemic toxicity of psi-tGel NPs, behavioral changes and histopathology of vital organs were carefully monitored in the psi-tGel NP-injected mice. No significant behavioral abnormalities were observed after the psi-tGel NPs were injected. The injection of psi-tGel NPs did not cause sudden death or shock-related responses. In the histologic examination, no discernible hemorrhage, infarction, or necrosis was observed in the vital organs (FIG. 6d). No apparent symptoms and histological lesions for severe systemic toxicity appeared in the psi-tGel NP-injected mice, and psi-tGel NPs were demonstrated to enable tumor-targeted siRNA delivery without systemic toxicity.

As is apparent from the foregoing examples, new tumor-targeted siRNA delivery was achieved using a gelatin nanocarrier. As natural gelatin rarely interacts with siRNA molecules due to its low binding affinity, the primary amines of gelatin and the 5'-end of the siRNA were thiol-modified. Under the optimized condition, the tGel spontaneously formed nanoparticles to form a complex with poly-siRNA molecules, and the resulting psi-tGel NPs protected the siRNA molecules from enzymatic degradation. Functional monomeric siRNA molecules were released from the nanoparticles in reductive conditions, and the psi-tGel NPs were effectively delivered to cytosol to down-regulate the target RFP gene. The psi-tGel NPs showed great tumor accumulation based on the EPR effect, and they induced effective target gene silencing in tumors with intravenous injection. In addition, no remarkable signs of systemic toxicity were observed in the psi-tGel NP-injected mice. The advantage of psi-tGel NPs for systemic siRNA delivery lies not only in their tumor-targeted delivery but also in their low toxicity. Thus, the present invention offers great potential for psi-tGel NPs as a safe and efficient system for siRNA delivery, and psi-tGel NPs can be further applicable to in vivo cancer therapy.

What is claimed is:

1. A gelatin-based nanoparticle complex for tumor-targeted delivery of siRNA, comprising:
   poly-siRNA chains whose ends are modified with thiol groups; and
   thiolated gelatin bound to the poly-siRNA chains through disulfide crosslinking and charge interactions.

2. The gelatin-based nanoparticle complex according to claim 1, wherein the thiolated gelatin is prepared by reacting gelatin with 10- to 50-fold molar excess of cystamine.

3. The gelatin-based nanoparticle complex according to claim 1, wherein the gelatin-based nanoparticle complex comprises 1 part by weight of the poly-siRNA chains and 5 to 20 parts by weight of the thiolated gelatin.

4. The gelatin-based nanoparticle complex according to claim 1, wherein the poly-siRNA has 21 to 1,000 base pairs (bp).

5. A method for preparing a gelatin-based nanoparticle complex for tumor-targeted delivery of siRNA, the method comprising:
   modifying a pair of complementary sequences of siRNA with thiol groups at the 5'-ends of the strands;
   mixing the pair of thiol-modified siRNA sequences with other pairs of thiol-modified siRNA sequences, followed by oxidation to form self-polymerized poly-siRNA chains;
   modifying gelatin with thiol groups to prepare thiolated gelatin; and
   reacting the poly-siRNA chains with the thiolated gelatin.

6. The method according to claim 5, wherein the thiolated gelatin is prepared by reacting gelatin with 10- to 50-fold molar excess of cystamine.

7. The method according to claim 5, wherein 1 part by weight of the poly-siRNA chains react with 5 to 20 parts by weight of the thiolated gelatin.

8. A gelatin-based nanoparticle complex for tumor-targeted delivery of siRNA, comprising:
   poly-siRNA chains whose ends are modified with thiol groups; and
   thiolated gelatin bound to the poly-siRNA chains through disulfide crosslinking and charge interactions;
   wherein the thiolated gelatin is prepared by reacting gelatin with 10- to 50-fold molar excess of cystamine.

* * * * *